US006674276B2

(12) United States Patent
Morgan et al.

(10) Patent No.: US 6,674,276 B2
(45) Date of Patent: Jan. 6, 2004

(54) SURFACE OBJECT LOCATOR WITH LEVEL INDICATOR AND SCRIBE TIP

(75) Inventors: Wayne D. Morgan, Milwaukee, WI (US); Chris W. Martin, New Berlin, WI (US); Thomas M. Luebke, Menomonee Falls, WI (US); David L. Wiesemann, Pewaukee, WI (US)

(73) Assignee: Actuant Corporation, Milwaukee, WI (US)

( * ) Notice: Subject to any disclaimer, the term of this patent is extended or adjusted under 35 U.S.C. 154(b) by 23 days.

(21) Appl. No.: 09/811,943

(22) Filed: Mar. 19, 2001

(65) Prior Publication Data

US 2002/0135347 A1 Sep. 26, 2002

Related U.S. Application Data

(63) Continuation-in-part of application No. 09/538,087, filed on Mar. 29, 2000, now Pat. No. 6,593,754.
(60) Provisional application No. 60/127,322, filed on Apr. 1, 1999.

(51) Int. Cl.$^7$ .................. G01R 19/00; G01V 3/165
(52) U.S. Cl. ............................................. 324/67
(58) Field of Search .................. 324/67, 326, 133, 324/529, 530, 556, 156, 157

(56) References Cited

U.S. PATENT DOCUMENTS

| 3,836,848 | A | * | 9/1974 | Blevins ................... 324/67 |
| 4,700,489 | A | * | 10/1987 | Vasile .................... 324/228 |
| 5,148,108 | A | * | 9/1992 | Dufour ................... 324/226 |
| 5,222,303 | A | * | 6/1993 | Jardine ................... 33/528 |
| D412,674 | S | * | 8/1999 | Kaiser ................... D10/65 |
| D419,546 | S | | 1/2000 | Krantz et al. |
| 6,211,662 | B1 | * | 4/2001 | Bijawat et al. ........... 324/67 |
| 6,215,293 | B1 | | 4/2001 | Yim |
| 2001/0007420 | A1 | * | 7/2001 | Bijawat et al. ........... 324/67 |

* cited by examiner

Primary Examiner—Jay Patidar
(74) Attorney, Agent, or Firm—Quarles & Brady LLP

(57) ABSTRACT

A housing for a subsurface object locator has a bubble level vial for leveling surfaces using the housing and a scribe tip for marking a surface being probed with the locator.

7 Claims, 3 Drawing Sheets

SURFACE OBJECT LOCATOR WITH LEVEL INDICATOR AND SCRIBE TIP

CROSS-REFERENCE TO RELATED APPLICATION

This application is a continuation-in-part of application Ser. No. 09/538,087 filed Mar. 29, 2000 now U.S. Pat. No. 6,593,754 which claims the benefit of U.S. Provisional Application No. 60/127,322 filed Apr. 1, 1999.

STATEMENT CONCERNING FEDERALLY SPONSORED RESEARCH OR DEVELOPMENT

Not applicable.

FIELD OF THE INVENTION

This invention relates to electronic instruments for detecting a stud or other object behind an opaque surface such as wallboard.

BACKGROUND OF THE INVENTION

Stud seekers for locating the position of wall studs behind wallboard material forming the wall surface are well known. They are used in hanging pictures, drilling holes and the like. The object of the present invention is to provide a housing for a stud seeker with improvements for marking the wall and leveling a picture or other wall hung object.

SUMMARY OF THE INVENTION

The invention provides improvements to a stud seeking housing that is, for example, in the overall shape of the housing disclosed in co-pending, commonly assigned U.S. patent application Ser. No. 09/538,087 filed Mar. 29, 2000. However, a stud seeker housing of the invention also has a bubble level vial attached to it so that one of the long edge surfaces of the housing can be placed against a surface of an object desired to be leveled and the vial used to adjust the orientation of the object. In addition, a housing of the invention may be provided with a scribe tip centrally located on or adjacent to the surface of the housing which is slid along the wall surface being probed and is capable of being used to put a small dent, hole, or scratch line in the surface.

In a preferred aspect, the bubble vial is provided on the front surface of the stud seeker housing parallel with the long edges of the housing and received in a recess which is molded into the housing. An adhesive may be used to hold the vial in the recess.

In another preferred aspect, the scribe tip is provided at a top end of the housing and raised slightly above the rear surface of the housing which is slid along the wall being probed. As such, the housing can be rotated about the top edge of the housing to bring the scribe tip into contact with the wall so as to create the mark in the wall.

The foregoing and other objects and advantages of the invention will appear in the detailed description which follows. In the description, reference is made to the accompanying drawings which illustrate a preferred embodiment of the invention.

DETAILED DESCRIPTION OF THE PREFERRED EMBODIMENT

Figure 1:
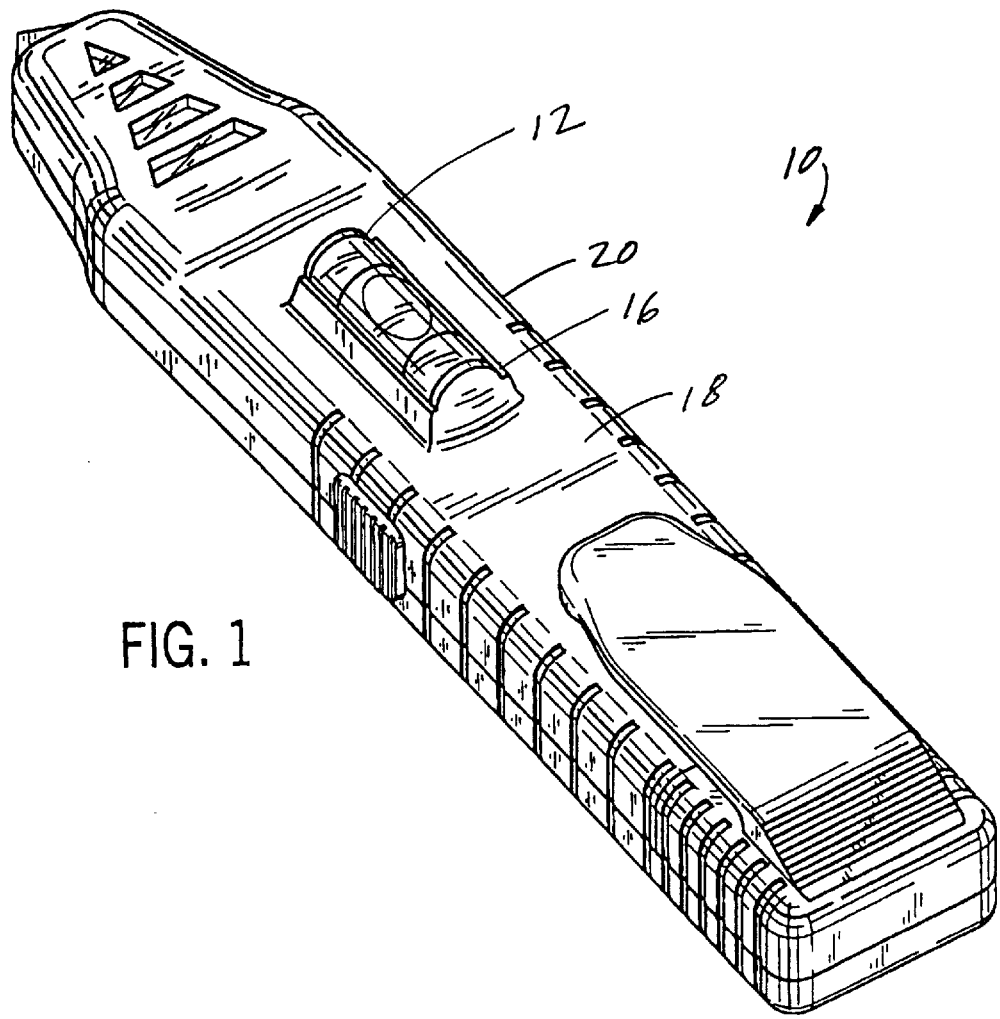
FIG. 1 is a perspective view of a stud seeker housing incorporating the invention.
Figures 5, 6:
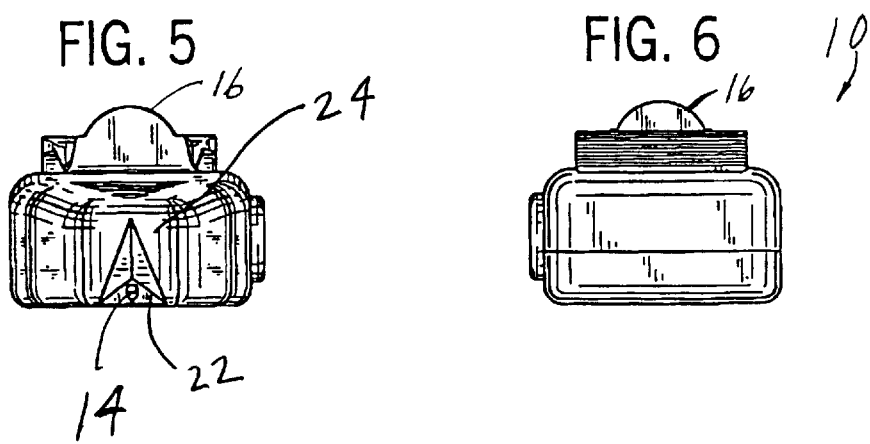
FIG. 5 is a top plan view of the housing.
FIG. 6 is a bottom plan view of the housing.

FIG. 1 illustrates a stud seeker housing 10 of the invention. In overall shape, geometry and circuitry, the stud seeker is the same as that described in U.S. patent application Ser. Nos. 09/538,087 and 09/538,088, both filed Mar. 29, 2000, and assigned to the assignee of the present application, the disclosures of which are hereby incorporated by reference. However, the housing 10 differs from the housing disclosed in the aforementioned applications because the housing 10 includes a bubble level vial 12 and a scribe tip 14.

Wall structures 16 are molded into the front surface 18 of the housing 10 so as to cradle the bubble level vial 12 in an orientation such that it is parallel with long side surface 20 of the housing 10. Vial 12 is secured in the structure 16 by any suitable means, for example, an adhesive. Cradle 16 also assures that the vial 12 is parallel with the side 20 to within acceptable limits. Thus, surface 20 can be placed against a surface desired to be leveled, for example, the top edge of a picture frame, and the picture frame leveled by centering the bubble in the vial 12.

Housing 10 also differs from the housing disclosed in the aforementioned applications by the fact that it includes the scribe tip 14. The scribe tip 14 is preferably made of a relatively hard and durable material, for example, metal, and may be insert molded into the pyramidal structure 22 which is molded on the top end surface 24 of the housing 10. The scribe tip 14 has a sharpened point which is directed toward the wall surface which would be probed by sliding the rear surface 26 along the surface to be probed. The tip 14, however, is raised above the level of the rear surface 26 so that the tip 14 would not touch the surface being probed while the surface 26 was held flat against the probed surface. However, the housing 10 with its surface 26 held against the probed wall surface can be rotated about edge 28, which exists between rear surface 26 and top surface 24, to bring the probe tip 14 into contact with the surface being probed and thereby make a mark in the surface being probed.

Figure 2:
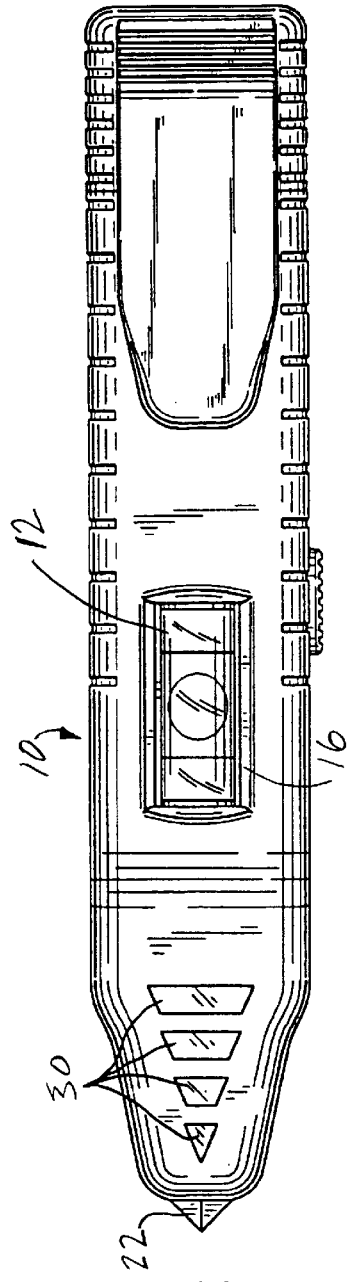
FIG. 2 is a top plan view of the housing.
Figure 3:
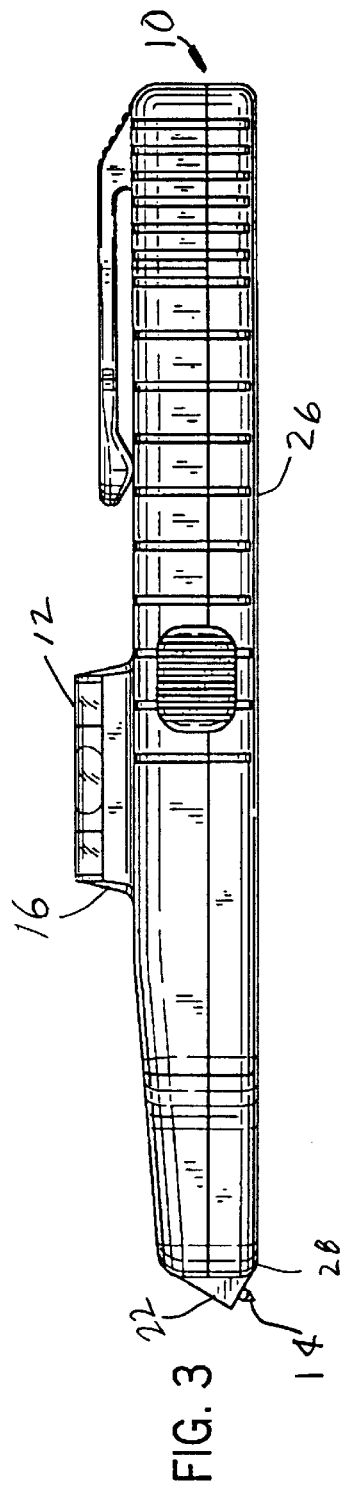
FIG. 3 is a left side plan view of the housing.
Figure 4:
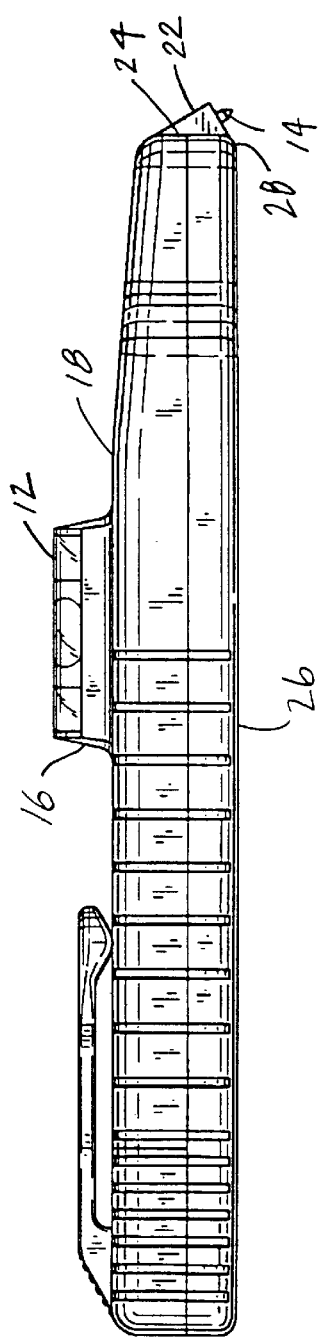
FIG. 4 is a right side plan view of the housing.
Figure 7:
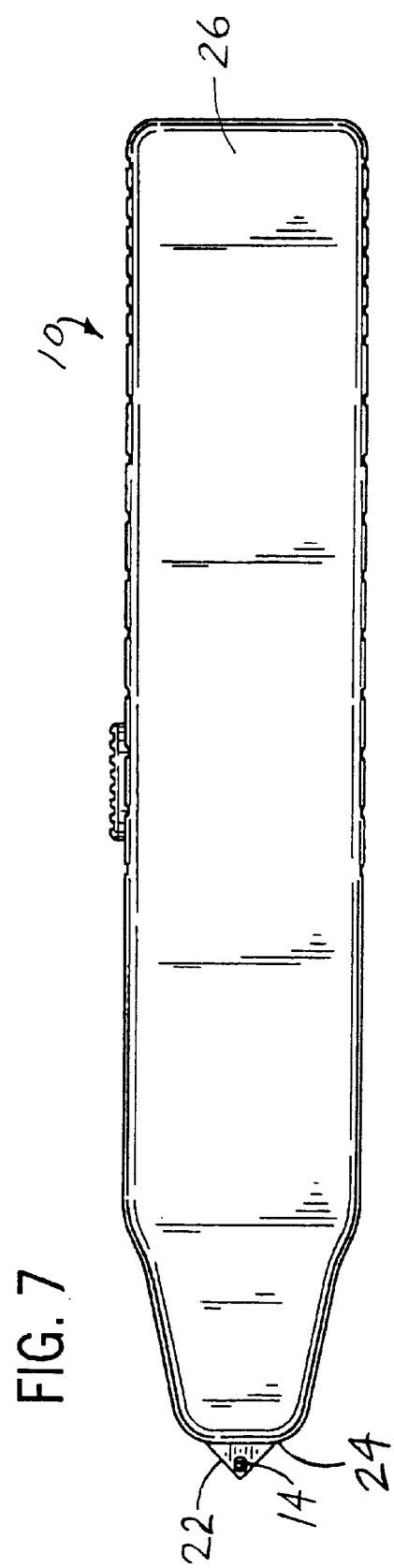
FIG. 7 is a rear plan view of the housing.

It is also noted that the probe tip 14 is at the lateral center of the housing 10, as best seen in FIG. 2. In fact, the pyramidal structure 22 is like an extension of the triangular array of indicators 30 which light up as a subsurface object is being approached. As seen in FIG. 2, the pyramidal structure 22 forms a point at the lateral center of the housing 10 which helps a user of the stud seeker identify the edge of a subsurface object, the presence of which is indicated by the indicators 30.

A preferred embodiment of a stud seeker housing of the invention has been described in considerable detail. Many modifications and variations to the preferred embodiment described will be apparent to those skilled in the art. Therefore, the invention should not be limited to the embodiment described, but should be defined by the claims which follow.

We claim:

1. In a hand-held subsurface object locator having a housing which contains circuitry for detecting a subsurface object behind a surface which is probed with the locator by sliding a detecting surface of the housing of the locator along the probed surface, the improvement wherein said housing has a scribe tip on a surface of the housing angled with respect to and adjacent to the detecting surface of the housing at an angle selected to prevent contact/with the probed surface as the locator is slid along the probed surface and rotatable about an edge of the detecting surface of the housing to contact the probed surface and mark a location of a detected object.

2. The improvement of claim 1, wherein said scribe tip is provided at a lateral center of said housing.

3. The improvement of claim 1, wherein said scribe tip is located adjacent to an end of said housing.

4. A hand-held subsurface object locator having a housing which contains circuitry for detecting a subsurface object behind a surface which is probed with the locator by sliding a detector surface of the locator along the surface which is probed, wherein the housing comprises:
   an electrical indicator activated by the circuitry as the locator approaches the subsurface object;
   a bubble level vial located along a flat surface of the housing for use in positioning a surface desired to be leveled; and
   a scribe tip located on the housing on a surface angled with respect to and adjacent to the detector surface of the housing such that the scribe tip does not contact the surface which is probed as the locator is slid along the surface, and so that the locator can be selectively rotated about an edge of the detector surface of the housing to mark a location of the detected object.

5. The handheld subsurface locator of claim 4, wherein the electrical indicator comprises a light.

6. The handheld subsurface locator of claim 4, further comprising a pyramidal structure molded on a top end surface of the housing, wherein the scribe tip is provided on the pyramidal structure.

7. The handheld subsurface locator of claim 5, wherein the light identifies an edge of the subsurface object for the user.

* * * * *

UNITED STATES PATENT AND TRADEMARK OFFICE
CERTIFICATE OF CORRECTION

PATENT NO. : 6,674,276 B2
DATED : January 6, 2004
INVENTOR(S) : Wayne D. Morgan et al.

It is certified that error appears in the above-identified patent and that said Letters Patent is hereby corrected as shown below:

Title page,
Item [54], Title, delete "SURFACE OBJECT LOCATOR WITH LEVEL INDICATOR AND SCRIBE TIP" and insert -- SUBSURFACE OBJECT LOCATOR WITH LEVEL INDICATOR WITH LEVEL INDICATOR ADN SCRIBE TIP --.

Column 3,
Line 2, after "housing at an angle" insert -- other than ninety degrees and --.
Line 2, after "prevent contact" insert -- of the tip --
Lines 3 and 5, after "probed surface" insert -- with the tip --.

Column 4,
Lines 3, after "surface of the housing" insert -- at an angle outer than ninety degrees --.
Line 7, after "detected object" insert -- with the scribe tip --.

Signed and Sealed this

Thirteenth Day of July, 2004

JON W. DUDAS
*Acting Director of the United States Patent and Trademark Office*